United States Patent [19]

Junino et al.

[11] Patent Number: 4,992,586

[45] Date of Patent: Feb. 12, 1991

[54] PROCESS FOR PREPARING 2-NITRO-META-PHENYLENEDIAMINES

[75] Inventors: Alex Junino, Livry-Gargan; Gerard Lang, Saint-Gratien; Nicole Jehanno, Brunoy; Jean J. Vandenbosche, Aulnay-sous-Bois, all of France

[73] Assignee: L'Oreal, Paris, France

[21] Appl. No.: 253,594

[22] Filed: Oct. 5, 1988

Related U.S. Application Data

[62] Division of Ser. No. 15,032, Feb. 17, 1987, Pat. No. 4,797,129.

[30] Foreign Application Priority Data

Feb. 14, 1987 [LU] Luxembourg .................... 86308

[51] Int. Cl.$^5$ ........................................ C07C 211/00
[52] U.S. Cl. .................... 564/367; 564/368; 564/369; 564/371; 564/441
[58] Field of Search ................ 564/406, 412, 441, 367

[56] References Cited

U.S. PATENT DOCUMENTS

| | | | |
|---|---|---|---|
| 3,586,725 | 6/1971 | Hunter | 564/406 X |
| 3,764,623 | 10/1973 | Hunter et al. | 564/441 |
| 3,895,934 | 7/1975 | Linder et al. | 564/441 X |
| 3,910,783 | 10/1975 | Hunter et al. | 564/441 X |
| 3,944,612 | 3/1976 | Bil | 564/406 X |
| 3,966,816 | 6/1976 | Woods et al. | 564/406 X |
| 4,101,582 | 7/1978 | Lutz et al. | 564/441 |
| 4,124,639 | 11/1978 | Lutz et al. | 564/441 |
| 4,207,261 | 6/1980 | Csikos | 564/406 |
| 4,482,742 | 11/1984 | Yamaguchi et al. | 564/412 |
| 4,704,474 | 11/1987 | Konrad et al. | 564/441 |
| 4,797,129 | 1/1989 | Junino et al. | 564/367 X |

OTHER PUBLICATIONS

Emerson, "Organic Reactions", vol. IV, pp. 175–177, 184–187 and 196–199 (1948).
Loudon, "Chemical Abstracts", vol. 35, pp. 1774 (1941).
Andrews, "Chemical Abstracts", vol. 74, p. 257, Section No. 6364h (1971).

*Primary Examiner*—Robert V. Hines
*Attorney, Agent, or Firm*—Cushman, Darby & Cushman

[57] ABSTRACT

A dye composition for keratinous fibers comprising a solvent and at least one dye which is a compound of formula:

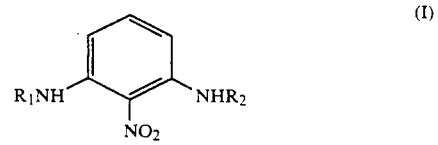

(I)

in which $R_1$ and $R_2$ are each, independently of each other, hydrogen, an alkyl group, a mono- or polyhydroxylated alkyl group, an alkyl group susbsituted by an alkoxy or hydroxyalkoxy group, or an aminoalkyl group, the amino group of which is optionally substituted with one or two alkyl or hydroxyalkyl groups, and it being possible for the nitrogen atom also to form part of a heterocyclic ring, all the abovementioned alkyl groups or moieties containing from 1 to 6 carbon atoms, or, if the compound of formula (I) contains an amino group which can be salified, a cosmetically acceptable salt thereof.

7 Claims, No Drawings

PROCESS FOR PREPARING 2-NITRO-META-PHENYLENEDIAMINES

This is a division of application Ser. No. 015,032, filed Feb. 17, 1987, patent No. 4,797,129.

The present invention relates to a dye composition for keratinous fibres based on 2-nitro-meta-phenylenediamines, to a process for dyeing keratinous fibres, especially human hair, using the dye composition, to a process for the preparation of these compounds, and to certain 2-nitro-meta-phenylenediamines employed.

It is known that nitro derivatives of the benzene series can be used to impart a direct coloration, or additional highlights in the case of oxidation dyeing, to keratinous fibres, especially to human hair.

The use, in direct dyeing, of 4-nitro-meta-phenylenediamines, which are yellow dyes, has already been proposed in French Pat. Nos. 1,508,405 and 1,584,965.

It is important, for colored highlights, to be able to produce warm shades such as copper, mahogany or red.

We have surprisingly found that 2-nitro-meta-phenylenediamines which, contrary to all expectations, are red to orange-red dyes, can be used to impart orange-red to red shades, which are useful warm shades, to keratinous fibres.

The dyes exhibit good solubility in the cosmetic media which are conventionally employed in hair dyeing and have the advantage of keeping well in the substrates which are usually employed in oxidation-dyeing compositions, especially in a reducing alkaline medium. This enables them to be combined with precursors of oxidation dyes to produce shades which are rich in highlights.

The present invention therefore provides a dye composition for keratinous fibres comprising a solvent and a tinctorially effective amount of at least one dye which is a compound of formula:

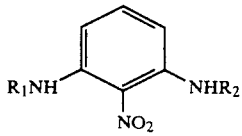

(I)

in which $R_1$ and $R_2$ are each, independently of each other, hydrogen, an alkyl group, a mono- or polyhydroxylated alkyl group, an alkyl group substituted by an alkoxy or hydroxyalkoxy group or an aminoalkyl group, the amino group of which is optionally substituted with one or two alkyl or hydroxyalkyl groups, and it being possible for the nitrogen atom of the aminoalkyl group to form part of a heterocyclic ring, all the abovementioned alkyl groups or moieties containing from 1 to 6 carbon atoms or, if the compound of formula (I) contains an amino group which can be salified, a cosmetically acceptable salt thereof.

Preferred alkyl groups or moieties have from 1 to 4 carbon atoms.

Preferred $R_1$ and $R_2$ groups are hydrogen and methyl, ethyl, n-propyl, n-butyl, β-hydroxyethyl, γ-hydroxypropyl, β-hydroxypropyl, β, γ-dihydroxypropyl, methoxyethyl, ethoxyethyl, β-hydroxyethoxyethyl, β-aminoethyl, β-hydroxyethylaminoethyl and β-diethylaminoethyl groups.

Compounds of formula (I) which are preferably employed in the dye composition of the invention include:
2,6-diaminonitrobenzene
2-(β-hydroxyethyl)amino-6-(β-hydroxyethyl)aminonitrobenzane
2-amino-6-methylaminonitrobenzene
2-amino-6-(β-hydroxyethyl)aminonitrobenzene
2-(γ-hydroxypropyl)amino-6-(γ-hydroxypropyl)aminonitrobenzene
2-(β-hydroxyethoxyethyl)amino-6-(β-hydroxyethoxyethyl)aminonitrobenzene
2-(β,γ-dihydroxypropyl)amino-6-(β, γ-dihydroxypropyl)aminonitrobenzene
2-(β-hydroxypropyl)amino-6-(β-hydroxypropyl)aminonitrobenzene
2-(β-methoxyethyl)amino-6-(β-methoxyethyl)aminonitrobenzene
2-(β-diethylaminoethyl)amino-6-(β-diethylaminoethyl)-aminonitrobenzene, and
2-(β-aminoethyl)amino-6-(β-aminoethyl)aminonitrobenzene.

The present invention also provides compounds of formula (I):

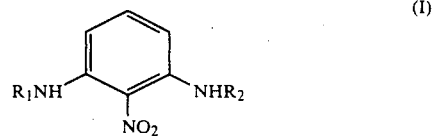

(I)

in which $R_1$ and $R_2$ have the abovementioned meanings provided that they are not simultaneously hydrogen.

The present invention also proves processes for preparing the compounds of formula (I).

The compounds of formula (I) may be prepared according to any one of three processes:

1st process:

This can only be applied to the preparation of compounds of formula (I) in which $R_2$ is other than hydrogen.

In a first step, a 2,6-dihalonitrobenzene of formula (IV) is reacted with an amine of formula $R_1NH_2$ or ammonia to produce a compound of formula (III) in which $R_1$ has the same meaning as above; the compound of formula (III) is then reacted with an amine of formula $R_2NH_2$, wherein $R_2$ has the same meaning as above, except for hydrogen, to produce a compound of formula (I) according to the following reaction scheme:

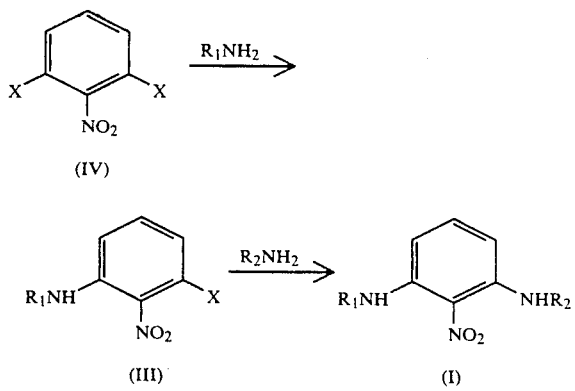

wherein $R_1$ and $R_2$ have the meanings indicated above and X is a halogen, preferably chlorine. Compounds of formula (I) in which $R_2$ is identical to $R_1$ can be produced directly by the action of an amine of formula $NH_2R_1$, wherein $R_1$ has the above meaning, except for hydrogen, on the compound of formula (IV).

The substitution of the halo groups by the amino groups $NHR_1$ and $NHR_2$ can be performed in the absence or presence of a solvent. Solvents which are generally employed include lower alcohols, dimethylformamide, dimethyl sulphoxide, N-methylpyrrolidone and N,N'-dimethyl-propyleneurea. In the case where ammonia or the amines $NH_2R_1$ or $NH_2R_2$ are employed in aqueous solution, it is preferable, for solubility reasons, to add a third solvent chosen from those mentioned above.

The reaction temperature is generally from 10° C. to the reflux temperature of aqueous ammonia, the amine $NH_2R_1$ and/or $NH_2R_2$, the solvent or the reaction mixture. The reaction temperature is preferably from 20° C. 170° C.

In the case of amines $NH_2R_1$ and/or $NH_2R_2$ having a boiling temperature lower than or equal to ambient temperature, or gaseous ammonia, the substitution may be performed in an autoclave, a pressure of 25 kg/cm² being generally sufficient.

Compounds of formula (III) in which $R_1$ is hydrogen, alkyl or hydroxyalkyl and X is chlorine can be prepared by reacting 2,6-dichloronitrobenzene and ammonia or the corresponding amine $NH_2R_1$ (see Beilstein, vol.12 p. 1648; JACS 61 (1939) p. 2658; JACS 64 (1942) p. 1285 and J. Org. Chem. vol. 42, No. 1, (1977) p. 166).

2,6-dihalonitrobenzenes can be prepared according to the processes which are described in the literature: for example, 2,6-dichloronitrobenzene may be prepared by oxidation of 2,6-dichloroaniline either with trifluoroperacetic acid, according to Organic Syntheses vol. 49, page 47, or with a solution of sodium perborate in acetic acid, according to Alexander McKillop and Jonathan A. Tarbin, Tetrahedron Letters, vol. 24, No. 14, pages 1505-1508 (1983).

Second process:

The compounds of formula (I) may be prepared from a 2,4,6-trihalonitrobenzene of formula (VI) which, in a first step, is reacted with an amine of formula $NH_2R_1$, wherein $R_1$ has the meaning specified above, or with ammonia, to produce a compound of formula (V) which, in a second step, is reacted with an amine of formula $NH_2R_2$ wherein $R_2$ is as defined above or ammonia to produce a compound of formula (II) in accordance with the following reaction scheme:

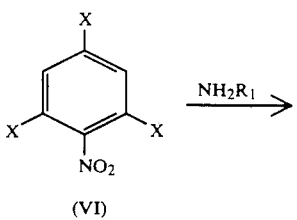

(VI)

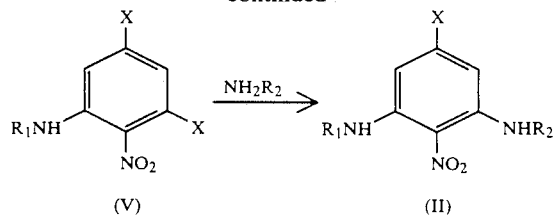

wherein $R_1$, $R_2$ and X have the meanings indicated above.

The compounds of formula (II) in which the group $R_2$ is identical with the group $R_1$ can be prepared in a single step from the compounds of formula (VI). The synthesis of 2,6-diamino-4-chloro-nitrobenzene by the reaction of ammonia with 2,4,6-trichloronitrobenzene is known (Beilstein, vol. 13, p.58).

The reaction conditions are similar to those described in the first process above. When the halogen is chlorine, simultaneous substitution of the chlorine by the $NHR_1$ group generally requires a shorter time and a lower temperature in the case of the compound of formula (VI) than in the case of the compound of formula (IV).

The compounds of formula (I) can be obtained by dehalogenation of the compounds (II), which dehalogenation may advantageously be carried out with the aid of triethylamine formate in the presence of palladium on charcoal, as described by N.A. Cortese and R.F. Heck in J. Org, Chem. vol. 42, No. 22, page 3491 (1977), or by any other method which does not involve the simultaneous reduction of the nitro group.

We have found that the dehalogenation reaction can be performed in the presence of a solvent such as an alcohol, dimethylformamide, N-methylpyrrolidone or acetic acid.

Palladium may be employed on a support such as barium sulphate, barium carbonate, alumina or calcium carbonate.

We have found it especially advantageous to use a palladium catalyst on calcium or barium carbonate in the presence of acetic acid, formic acid and triethylamine.

The compounds produced using this method are of greater purity than those produced by the method described in J. Org. Chem., vol. 42, No. 22, page 3491 (1977).

The 2,4,6-trihalonitrobenzenes can be prepared according to the methods described in the literature: for example, 2,4,6-trichloronitrobenzene may be prepared by oxidation of 2,4,6-trichloroaniline either with trifluoro-peracetic acid, according to Organic Syntheses Vol. 49, page 47, or with a solution of sodium perborate in acetic acid, according to Alexander McKillop and Jonathan A. Tarbin, Tetrahedron Letters, Vol. 24, No. 14, page 1505-1508 (1983).

The compound of formula (I) in which $R_1$ and $R_2$ are both hydrogen may also be prepared from 2-nitroisophthalic acid according to the process described in J.C.S. Perkin Trans. 2 (3), page 590, (1981).

Third process:

2,6-diaminonitrobenzene is subjected to conventional chemical alkylation, hydroxyalkylation or aminoalkylation to produce a compound of formula (I) in which $R_1$ and/or $R_2$ are other than hydrogen. These alkylation, hydroxyalkylation or aminoalkylation processes are described, for example, in French Pat. Nos. 2,348,911, 2,497,662 and 2,492,370.

The compounds of formula (I) which are more particularly preferred according to the present invention are:

2-($\beta$-hydroxyethyl)amino-6-($\beta$-hydroxyethyl)aminonitro-benzene,
2-amino-6-methylaminonitrobenzene,
2-amino-6-($\beta$-hydroxyethyl)aminonitrobenzene
2-($\gamma$-hydroxypropyl)amino-6-($\gamma$-hydroxypropyl)aminonitrobenzene,
2-($\beta$-hydroxyethoxyethyl)amino-6-($\beta$-hydroxyethoxyethyl)-aminonitrobenzene,
2-($\beta,\gamma$-dihydroxypropyl)amino-6-($\beta,\gamma$-dihydroxypropyl)-aminonitrobenzene,
2-($\beta$-hydroxypropyl)amino-6-($\beta$-hydroxypropyl)amino-nitrobenzene,
2-($\beta$-methoxyethyl)amino-6-($\beta$-methoxyethyl)aminonitro-benzene,
2-($\beta$-diethylaminoethyl)amino-6-($\beta$-diethylaminoethyl)-aminonitrobenzene, and
2-($\beta$-aminoethyl)amino-6-($\beta$-aminoethyl)aminonitrobenzene.

The dye compositions according to the present invention generally contain the compounds of formula (I) in a proportion of from 0.001 to 5% by weight, preferably from 0.05 to 2% by weight, relative to the total weight of the composition.

The solvent is preferably a cosmetic vehicle comprising water, but it is also possible to add organic solvents to the compositions in order to dissolve compounds which might not be sufficiently soluble in water. Examples of such solvents are lower alkanols (e.g. containing up to 6 or up to 4 carbon atoms) such as ethanol and isopropanol, aromatic alcohols such as benzyl alcohol or phenoxyethanol, polyols such as glycerol and glycols and glycol ethers such as 2-butoxyethanol or 2-ethoxyethanol, ethylene glycol, propylene glycol, diethylene glycol monomethyl ether and monoethyl ether. These solvents are preferably present in a proportion of from 1 to 75% by weight, particularly from 5 to 50% by weight, relative to the total weight of the composition.

The compositions may contain anionic, cationic, nonionic or amphoteric surface-active agents or mixtures thereof. These surface-active products are generally present in the compositions of the invention in a proportion of from 0.5 to 55% by weight, preferably from 4 to 40% by weight, relative to the total weight of the composition.

The compositions may be thickened, preferably with sodium alginate, gum arabic, xanthane gum, cellulose derivatives such as methylcellulose, hydroxyethylcellulose, hydroxypropylmethylcellulose or carboxymethylcellulose, or a polymer which acts as a thickener such as an acrylic acid derivative. Inorganic thickening agents such as bentonite can also be used. These thickening agents are preferably present in a proportion of from 0.1 to 10% by weight, particularly from 0.5 to 2% by weight, relative to the total weight of the composition.

The compositions according to the invention may also contain various adjuvants commonly employed in hairdyeing compositions, and in particular penetrating agents, dispersing agents, sequestering agents, film-forming agents, buffers and/or perfumes.

These compositions may be presented in various forms such as liquids, creams, gels or any other appropriate form for performing hair dyeing. They may be packaged with a propellent agent in aerosol bottles.

The pH of the dye compositions is generally from 3 to 11.5, preferably from 5 to 11.5. It can be adjusted to the required value with an alkalizing agent such as aqueous ammonia, sodium, potassium or ammonium carbonate, sodium or potassium hydroxide, an alkanolamine such as mono-, di- or triethanolamine, 2-amino-2-methyl-1-propanol, 2-amino-2-methyl-1,3-propanediol, or an alkylamine such as ethylamine or triethylamine, or with an acidifying agent such as phosphoric, hydrochloric, tartaric, acetic, lactic or citric acid.

When the compositions are intended to be used in a direct hair-dyeing process, they may additionally contain at least one direct dye other than that of formula (I) or a salt thereof, such as an azo or anthraquinone dye, for example 1,4,5,8-tetraaminoanthraquinone, an indophenol, an indoaniline or a nitro dye of the benzene series.

The concentration of the direct dyes is generally from 0.001 to 5% by weight relative to the total weight of the composition.

The present invention also provides a method of dyeing keratinous fibres, especially human hair, wherein a dyeing composition as defined above is applied to the fibres.

The compositions can be used in a direct dyeing process and can, for example, be applied to the keratinous fibres for from 5 to 50 minutes, and the fibres are rinsed, washed if desired optionally using a shampoo, rinsed again and dried.

The compositions according to the present invention may also be used in the form of hairsetting lotions intended to impart a slight coloration or highlights to the hair and to improve the set retention. In this case, they are generally in the form of aqueous, alcoholic or aqueous alcoholic solutions containing at least one cosmetic resin and they can be applied to previously washed and rinsed damp hair which, if desired, is wound on rollers and is then dried.

Examples of cosmetic resins include polyvinylpyrrolidone, crotonic acid-vinyl acetate or vinylpyrrolidone-vinyl acetate copolymers, copolymers of half-esters of maleic anhydride with butyl vinyl ether or of maleic anhydride with methyl vinyl ether, copolymers of maleic acid with methyl or butyl vinyl ethers, as well as any other cationic, anionic, nonionic or amphoteric polymer usually employed in a composition of this type. These cosmetic resins generally are present in a proportion of from 0.1 to 4% by weight, preferably from 0.5 to 3% by weight, based on the total weight of the composition.

When the compositions according to the invention form oxidation dye compositions involving development with an oxidizing agent, the compounds of formula (I) are intended to impart highlights to the final dye.

Thus the dye composition comprising a solvent and at least one compound of formula (I) or a salt thereof can be used in the direct dyeing of keratinous fibres or for the oxidation dyeing of these fibres, in which case the compounds of formula (I) impart additional highlights to the basic color obtained by oxidizing development of the oxidation dye precursors.

These compositions contain precursors of oxidation dyes in combination with at least one nitro dye of formula (I) and, if desired, other direct dyes.

They may, for example, contain para-phenylenediamines such as para-phenylenediamine, para-tolylenediamine, 2-chloro-para-phenylenediamine, 2,6-dimethylparaphenylenediamine, 2,6-dimethyl-3-methoxy-paraphenylenediamine, N-(β-methoxyethyl)-paraphenylenediamine, N, N-(β-hydroxyethyl)-paraphenylenediamine N-(ethyl,carbamylmethyl)-4-aminoaniline or salts thereof.

They may also contain para-aminophenols, for example para-aminophenol, N-methyl-para-aminophenol, 2-chloro-4-aminophenol, 3-chloro-4-aminophenol, 2-methyl-4-aminophenol, or their salts or ortho-aminophenol.

They may also contain heterocyclic derivatives such as 2,5-diaminopyridine or 7-aminobenzomorpholine.

The compositions may contain, in combination with the precursors of oxidation dyes, couplers which are well known in the state of the art.

Examples of such couplers include meta-diphenols, meta-aminophenols and their salts, meta-phenylenediamines and their salts, meta-acylaminophenols, meta-ureidophenols, meta-carbalkoxyaminophenols, α-naphthol, couplers containing an active methylene group, such as diketone compounds and pyrazolones and heterocyclic couplers derived from pyridine and from benzomorpholine.

In addition these compositions may contain a reducing agent, which is generally present in a proportion of from 0.05 to 3% by weight relative to the total weight of the composition.

The oxidation dye precursors are preferably employed in the compositions of the invention in a concentration of from 0.001 to 5% by weight, more preferably from 0.03 to 2% by weight, based on the total weight of the composition. The couplers are preferably present in a proportion of from 0.001 to 5% by weight, more preferably from 0.015 to 2% by weight. The pH of the oxidation dye compositions is preferably from 7 to 11.5 and may be adjusted with an alkalizing agent as defined above.

The process of dyeing keratinous fibres, especially human hair, employing development by means of an oxidizing agent, consists in applying to the hair a dye composition according to the invention. The development of the color may then take place slowly in the presence of atmospheric oxygen, but preferably a chemical development system is used. In most cases it is hydrogen peroxide, urea peroxide or a persalt. In particular, a 20-volume hydrogen peroxide solution can be used.

Once the composition containing the oxidizing agent has been applied to the keratinous fibres, it is left in place for from 10 to 50 minutes, preferably from 15 to 30 minutes, after which the keratinous fibres are rinsed, washed with a shampoo if desired and are rinsed again and dried.

The examples which follow further illustrate the present invention.

REFERENCE EXAMPLE

Preparation of 2,6-diaminonitrobenzene

First step

Preparation of 4-chloro-2,6-diaminonitrobenzene

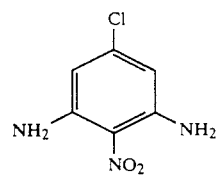

0.34 mole (76 g) of 2,4,6-trichloronitrobenzene is added, in an autoclave, to 400 ml of 28% strength aqueous ammonia in water and 100 ml of ethanol. The reaction mixture is heated for 16 hours at 155°–160° C., the pressure being 20 kg/cm$^2$. The expected product precipitates after cooling. After filtration and reslurrying in water until the aqueous washes are neutral, it is dried in vacuum in the presence of phosphorus pentoxide. After recrystallization from isopropanol, in order to remove a gum, it melts at 202° C. (literature 192 °–194° C).

Analysis of the product obtained gives the following results:

| Analysis | Calculated for C$_6$H$_6$ClN$_3$O$_2$ | Found |
|---|---|---|
| C % | 38.40 | 38.55 |
| H % | 3.20 | 3.26 |
| N % | 22.40 | 22.43 |
| O % | 17.06 | 16.88 |
| Cl % | 18.93 | 18.74 |

Second step

Preparation of 2,6-diaminonitrobenzene 68 mg of palladium at a concentration of 10% on charcoal are added to 0.016 mole (3 g) of 4-chloro-2,6-diaminonitro-benzene in 6 ml of triethylamine, and 1.32 ml of formic acid are then added dropwise. A high exothermicity is noted. The reaction medium is heated to 90° C. for 1 hour 30. After dilution of the reaction mixture with ethanol, the catalyst is removed by hot filtration. The filtrate, evaporated to dryness under reduced pressure, enables a dry extract to be obtained. After dilution of the dry extract with water, the expected product precipitates. After filtration and washing with water, followed by drying under vacuum in the presence of phosphorus pentoxide, it is recrystallized from toluene. It melts at 142° C. (literature 141° C., 145° C.).

Analysis of the product obtained gives the following results:

| Analysis | Calculated for C$_6$H$_7$N$_3$O$_2$ | Found |
|---|---|---|
| C % | 47.06 | 47.28 |
| H % | 4.57 | 4.58 |
| N % | 27.45 | 27.35 |
| O % | 20.91 | 20.80 |

EXAMPLE 1

Preparation of 2-(β-hydroxyethyl)amino-6-(β-hydroxyethyl)aminonitrobenzene (Second process)

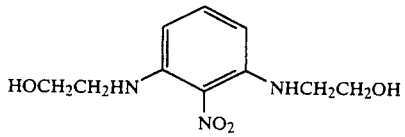

First step

Preparation of 4-chloro-2-(β-hydroxyethyl)amino-6-(β-hydroxyethyl)aminonitrobenzene 0.132 mole (30 g) of 2,4,6-trichloronitrobenzene is heated to 95° C. in 120 ml of ethanolamine. After 30 minutes, the reaction mixture is poured onto 240 g of a mixture of ice and water. The expected product precipitates. It is filtered off, washed with water and then dried under vacuum in the presence of phosphorus pentoxide. After recrystallization from absolute ethanol, it melts at 154° C.

Analysis of the product obtained gives the following results:

| Analysis | Calculated for $C_{10}H_{14}ClN_3O_4$ | Found |
|---|---|---|
| C % | 43.56 | 43.37 |
| H % | 5.08 | 5.11 |
| N % | 15.24 | 15.25 |
| O % | 23.23 | 23.45 |
| Cl % | 12.88 | 13.01 |

Second step

Preparation of 2-(β-hydroxyethyl)amino-6-β-hydroxyethyl)aminonitrobenzene 354 mg of palladium at a concentration of 10% on charcoal are added to 0.084 mole (23.1 g) of 4-chloro-2-(β-hydroxyethyl)amino-6-(β-hydroxyethyl)aminonitrobenzene in 23.7 g of triethylamine. 7 ml of formic acid are then run in dropwise. A high exothermicity is noted. The reaction mixture is heated to 70° C. for 1 hour 30. After dilution of the reaction mixture with ethanol, the catalyst is removed by hot filtration. The filtrate, evaporated to dryness under reduced pressure, enables a dry extract to be obtained. After dilution of the dry extract with water, the expected product precipitates. After being filtered off, washed with water and then dried under vacuum in the presence of phosphorus pentoxide, it is recrystallized twice from isopropanol. It melts at 103°-104° C., resolidifies and then melts at 112°-113° C.

Analysis of the product obtained gives the following results:

| Analysis | Calculated for $C_{10}H_{15}N_3O_4$ | Found |
|---|---|---|
| C % | 49.78 | 49.66 |
| H % | 6.27 | 6.28 |
| N % | 17.42 | 17.40 |
| O % | 26.53 | 26.46 |

EXAMPLE 2

Preparation of 2-(β-hydroxyethyl)amino-6-(β-hydroxyethyl)aminonitrobenzene (First process)

0.25 mole (48 g) of 2,6-dichloronitrobenzene, prepared according to the method described by Alexander McKillop and Jonathan A. Tarbin in Tetrahedron Letters, Vol. 24 No. 14, page 1505 (1983), is added to 200 ml of ethanolamine. The mixture is heated to 98° C. for 8 hours. The reaction mixture is poured onto ice. After phase separation, the precipitate is taken up in the minimum quantity of ethanol, with stirring. After dilution with a mixture of ice and water, the expected product is filtered off, washed with water and then recrystallized from ethanol. It is identical with the product prepared in Example 1.

EXAMPLE 3

Preparation of 2-amino-6-methylaminonitrobenzene (Second process)

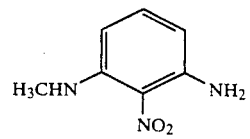

First step

Preparation of 4-chloro-2-amino-6-methylaminonitrobenzene

First stage

Preparation of 2,4-dichloro-6-methylaminoitrobenzene 0.150 mole (34 g) of 2,4,6-trichloronitrobenzene is added portionwise, at ambient temperature, to 300 ml of a 30% strength solution of methylamine in absolute ethanol. After stirring for 23 hours at ambient temperature, a precipitate, consisting essentially of 4-chloro-2-methylamino-6-methylaminonitrobenzene, is removed by filtration. The filtrate is evaporated to dryness under reduced pressure. 800 ml of concentrated hydrochloric acid are added to the dry extract obtained in this manner. The insoluble fraction is removed by filtration. After dilution of the filtrate with 650 ml of water, the expected product precipitates. It is washed with water and is then dried under vacuum in the presence of phosphorus pentoxide. After recrystallization from isopropanol and then from absolute ethanol, it melts at 120° C.

Analysis of the product obtained gives the following results:

| Analysis | Calculated for $C_7H_6Cl_2N_2O_2$ | Found |
|---|---|---|
| C % | 38.01 | 38.02 |
| H % | 2.71 | 2.72 |
| N % | 12.67 | 12.77 |
| O % | 14.48 | 14.40 |
| Cl % | 32.13 | 32.01 |

Second stage

Preparation of 4-chloro-2-amino-6-methylaminonitrobenzene 0.034 mole (7.5 g) of 2,4-dichloro-6-methylaminonitrobenzene is added in an autoclave to 100 ml of a 28% strength solution of ammonia in water and 50 ml of ethanol. The reaction mixture is heated to 145°-150° C. for 12 hours, the pressure being 12 kg/cm². After cooling, the expected product precipitates from the reaction mixture. After being filtered off and reslurried in water, it is dried hot under vacuum in the presence of phosphorus pentoxide. Recrystallized from isopropanol, it melts at 129° C.

Analysis of the product obtained gives the following results:

| Analysis | Calculated for $C_7H_8ClN_3O_2$ | Found |
|---|---|---|
| C % | 41.69 | 41.71 |
| H % | 3.97 | 4.02 |
| N % | 20.84 | 20.80 |
| O % | 15.88 | 15.92 |
| Cl % | 17.62 | 17.49 |

Second step

Preparation of 2-amino-6-methylaminonitrobenzene 59.5 mg of palladium at a concentration of 10% on charcoal are added to 0.014 mole (2.8 g) of 4-chloro-2-amino-6-methylaminonitrobenzene in 5.3 ml of triethylamine, and 1.16 ml of formic acid are then run in dropwise. A high exothermicity is noted. The reaction mixture is heated to 80° C. for 40 minutes. After dilution of the reaction mixture with ethanol, the catalyst is removed by hot filtration. The filtrate, evaporated under reduced pressure, enables a dry extract to be obtained. After dilution of the dry extract with water, the expected product precipitates. After being filtered off and washed with water, the precipitate is dried under vacuum in the presence of phosphorus pentoxide. After two recrystallizations from isopropanol in order to remove a gum, the product melts at 70° C.

Analysis of the product obtained gives the following results:

| Analysis | Calculated for $C_7H_9N_3O_2$ | Found |
|---|---|---|
| C % | 50.30 | 50.19 |
| H % | 5.39 | 5.38 |
| N % | 25.15 | 25.12 |
| O % | 19.16 | 19.42 |

EXAMPLE 4

Preparation of 2-amino-6-(β-hydroxyethyl)aminonitrobenzene (Third process)

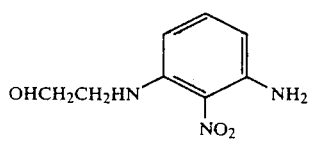

First step

Preparation of β-chloroethyl N-[(3-amino-2-nitro)phenyl]carbamate 7.5 ml of β-chloroethyl chloroformate are added dropwise over 20 minutes to a mixture of 0.066 mole (10 g) of 2,6-diaminonitrobenzene (reference example) and of 0.036 mole (3.6 g) of calcium carbonate in 50 ml of diethylene glycol dimethyl ether (diglyme) heated to 80° C. Heating is continued for 1 hour after the addition is complete. The reaction mixture is diluted with a mixture of ice and water. The expected product precipitates. When dried hot under vacuum and recrystallized from isopropyl ether and isopropyl alcohol, it melts at 92° C.

Second step

Preparation of N-[(3'-amino-2'-nitro)phenyl]-1, 3-oxazolidin-2-one 3 ml of a 30% strength solution of sodium methylate in methanol are added slowly to a suspension of 0.015 mole (4 g) of the compound prepared in the first step in absolute ethanol. The temperature of the reaction mixture reaches 35° C. The expected product precipitates during the addition. After being reslurried in water and then dried under vacuum in the presence of phosphorus pentoxide, it melts at 132° C.

Third step

Preparation of 2-amino-6-(β-hydroxyethyl) aminonitrobenzene 4.5 ml of a 5N sodium hydroxide solution are added dropwise to a solution of 0.011 mole (2.5 g) of the compound prepared in the preceding step in 10 ml of ethanol at 90° C. Heating is continued for one hour. The inorganic salts formed are removed by filtration of the reaction mixture. The aqueous alcoholic filtrate is evaporated to dryness under vacuum. Water is added to the dry residue obtained in this manner; after being acidified, the expected product precipitates. After being filtered off and then dried under vacuum it is recrystallized from isopropyl alcohol. It melts at 129° C.

Analysis of the product obtained gives the following results:

| Analysis | Calculated for $C_{18}N_{11}N_3O_3$ | Found |
|---|---|---|
| C % | 48.72 | 48.86 |
| H % | 5.62 | 5.45 |
| N % | 21.31 | 21.26 |
| O % | 24.34 | 24.59 |

EXAMPLE 5

Preparation of 2-(γ-hydroxypropyl)amino-6-(γ-hy-droxypropyl)aminonitrobenzene (Second process)

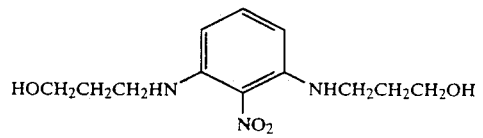

First step

Preparation of 4-chloro-2-(γ-hydroxypropyl)amino-6-(γ-hydroxypropyl)aminonitrobenzene

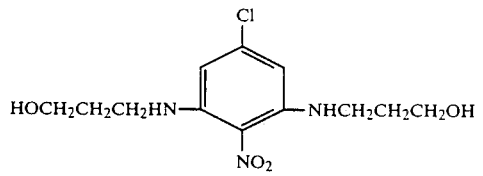

0.22 mole (50 g) of 2,4,6-trichloronitrobenzene is added portionwise, with stirring, to 150 ml of 3-amino-1-propanol, heated to 80° C. After the end of the addition, heating is continued for 1 hour 30 minutes. The reaction mixture is poured onto 300 g of iced water. An oil is obtained, which crystallizes after addition of concentrated hydrochloric acid. The precipitate of the expected product is filtered off, and is washed with a 2N solution of hydrochloric acid and then with water to neutrality. After being dried at 40° C. in the presence of phosphorus pentoxide, it is recrystallized from 96° ethanol. It melts at 127° C.

Analysis of the product obtained gives the following results:

| Analysis | Calculated for $C_{12}H_{18}N_3O_4Cl$ | Found |
|---|---|---|
| C % | 47.45 | 47.41 |
| H % | 5.97 | 6.01 |
| N % | 13.83 | 13.99 |
| O % | 21.07 | 20.98 |
| Cl % | 11.67 | 11.89 |

Second step

Preparation of 2-(γ-hydroxypropyl)amino-6-(γ-hydroxypropyl)aminonitrobenzene 340 mg of palladium at a concentration of 10% on calcium carbonate are added to 0.017 mole (5.2 g) of 4-chloro-2-(γ-hydroxypropyl)amino-6-(γ-hydroxypropyl)amino-nitrobenzene in 11.7 ml of triethylamine. 0.9 ml of acetic acid and 2.3 ml of formic acid are then run in dropwise. A high exothermicity is noted. The reaction mixture is heated under reflux for 3 hours. 10 ml of water are added. The reaction mixture diluted in this manner is filtered hot to remove the catalyst. The expected product precipitates from the filtrate as it cools. It is filtered off, washed with water and then dried under vacuum in the presence of phosphorus pentoxide. Recrystallized from ethyl acetate, it melts at 90° C.

Analysis of the product obtained gives the following results:

| Analysis | Calculated for $C_{12}H_{19}N_3O_4$ | Found |
|---|---|---|
| C % | 53.52 | 53.60 |
| H % | 7.11 | 7.08 |
| N % | 15.60 | 15.70 |
| O % | 23.77 | 23.71 |

EXAMPLE 6

Preparation of 2-(β-hydroxyethoxyethyl)amino-6-(β-hydroxyethoxyethyl)aminonitrobenzene (Second process)

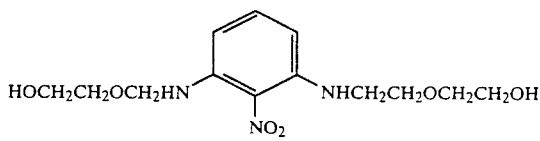

First step

Preparation of 4-chloro-2(β-hydroxyethoxyethyl)-amino-6-(β-hydroxyethoxyethyl)aminonitrobenzene

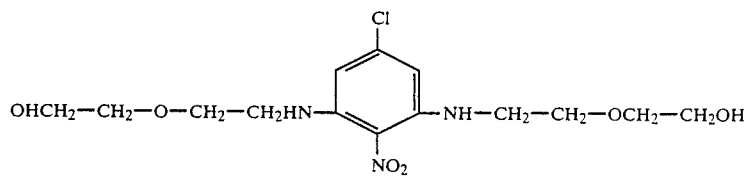

A mixture consisting of 0.1 mole (22.6 g) of 2,4,6-trichloronitrobenzene, 0.6 mole (63 g) of 2-(β-aminoethoxy)ethanol and 20 ml of dioxane is heated under reflux. After 4 hours, the reaction mixture is poured onto 200 g of ice. After being acidified with concentrated hydrochloric acid, the expected product crystallizes out. After filtration, washing with water and drying hot under vacuum, the product is recrystallized from acetonitrile and then from toluene. It melts at 83° C.

Analysis of the product obtained gives the following results:

| Analysis | Calculated for $C_{14}H_{22}N_3O_6Cl$ | Found |
|---|---|---|
| C % | 46.22 | 45.93 |
| H % | 6.10 | 6.08 |
| N % | 11.55 | 11.79 |
| O % | 26.39 | 26.41 |
| Cl % | 9.74 | 9.81 |

Second step

Preparation of 2-(β-hydroxyethoxyethyl)amino-6-(β-hydroxyethoxyethyl)aminonitrobenzene 300 mg of palladium at a concentration of 10% on calcium carbonate are added to 0.015 mole (5.45 g) of 4-chloro-2-(β-hydroxyethoxyethyl)amino-6-(β-hydroxyethoxyethyl)aminonitrobenzene in 11 ml of triethylamine. 1.1 ml of acetic acid and 2.05 ml of formic acid are then run in dropwise. When the additions have been completed the reaction mixture is heated under reflux for 30 minutes. 10 ml of water are added. The reaction mixture diluted in this manner is filtered hot to remove the catalyst. The filtrate is evaporated to dryness under vacuum in the presence of absolute ethanol and the residue is taken up with ethyl acetate. Insoluble organic salts are removed by filtration. The ethyl acetate is evaporated off to dryness. Acetonitrile and then water are added to the residue. The expected product precipitates. Recrystallized from ethyl acetate, it melts at 82° C.

Analysis of the product obtained gives the following results:

| Analysis | Calculated for $C_{14}H_{23}N_3O_6$ | Found |
|---|---|---|
| C % | 51.05 | 51.12 |
| H % | 7.04 | 6.99 |
| N % | 12.76 | 12.99 |
| O % | 29.15 | 28.91 |

EXAMPLE 7

Preparation of 2-(β,γ-dihydroxypropyl)amino-6-(β,γ-dihydroxypropyl)aminonitrobenzene (Second process)

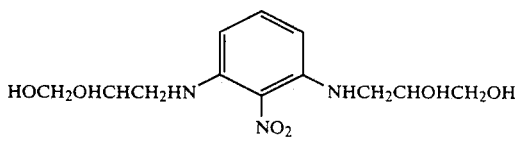

First step
Preparation of 4-chloro-2-(β,γ-dihydroxypropyl)-amino-6-(β,γ-dihydroxypropyl)aminonitrobenzene

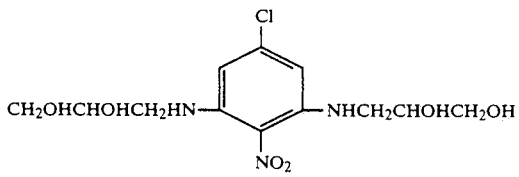

The mixture consisting of 0.1 mole (22.6 g) of 2,4,6-trichloronitobenzene and 54.7 g of 3-amino-1,2-propanediol in 20 ml of dioxane is heated under reflux. After 4 hours' heating, the dioxane is evaporated off under reduced pressure. The oil obtained is diluted with approximately 300 ml of water. The expected product is obtained by chromatography under pressure, in two operations. Approximately 200 ml of the aqueous solution of the expected product containing 3-amino-1,2-propanediol are injected into a $C_{18}RD$ chromatography column (Waters Prep 500 Apparatus). The expected product is eluted with a solution containing 35% of methanol and 65% of water. After the fractions containing the expected product have been evaporated down, a dry extract is obtained, which is recrystallized from 96° alcohol.

The product obtained melts at 146° C.
Elemental analysis of the product obtained gives the following results:

| Analysis | Calculated for $C_{12}H_{18}N_3O_6Cl$ | Found |
|---|---|---|
| C % | 42.92 | 42.87 |
| H % | 5.36 | 5.37 |
| N % | 12.52 | 12.39 |
| O % | 28.61 | 28.69 |
| Cl % | 10.58 | 10.47 |

Second step
Preparation of 2-(β,γ-dihydroxypropyl)amino-6-(β,γ-dihydroxypropyl)aminonitrobenzene
240 mg of palladium at a concentration of 10% on calcium carbonate are added to 0.012 mole (4 g) of 4-chloro-2-(β,γ-dihydroxypropyl)amino-6-(β,γ-dihydroxypropyl)-aminonitrobenzene in 8.6 ml of triethylamine. 0.8 ml of acetic acid and 1.65 ml of formic acid are then added dropwise. The reaction mixture is heated under reflux for 7 hours. 10 ml of water are added. The reaction mixture diluted in this manner is filtered hot to remove the catalyst. The filtrate is evaporated to dryness under vacuum in the presence of absolute ethanol. The residue is dissolved in the minimum quantity of water. The expected product is extracted with ethyl acetate. The ethyl acetate phases are evaporated to dryness, after drying over sodium sulphate. After a small quantity of water has been added to the oil obtained, the expected product precipitates. Recrystallized from ethyl acetate, it melts at 138° C.

Analysis of the product obtained gives the following results:

| Analysis | Calculated for $C_{12}H_{19}N_3O_6$ | Found |
|---|---|---|
| C % | 47.83 | 47.86 |
| H % | 6.36 | 6.36 |
| N % | 13.95 | 14.13 |
| O % | 31.86 | 31.89 |

EXAMPLE 8

Preparation of 2-(β-hydroxypropyl)amino-6-(β-hydroxypropyl)aminonitrobenzene (Second process)

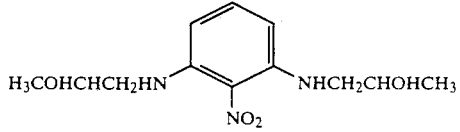

First step
Preparation of 4-chloro-2-(β-hydroxypropyl)amino-6-(β-hydroxypropyl)aminonitrobenzene

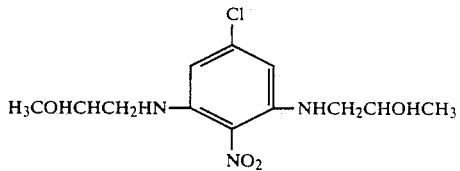

0.2 mole (45.3 g) of 2,4,6-trichloronitrobenzene is added in small portions, with stirring, to 180 ml of 3-amino-2-propanol, heated to 80° C. The reaction is exothermic. After 3 hours 30 minutes' heating, the reaction mixture is poured onto 180 ml of iced water. The expected product precipitates. It is filtered off, washed with water to neutrality and then dried under vacuum in the presence of phosphorus pentoxide. After recrystallization from 96° ethanol, it melts at 170° C.

Analysis of the product obtained gives the following results:

| Analysis | Calculated for $C_{12}H_{18}N_3O_4Cl$ | Found |
|---|---|---|
| C % | 47.45 | 47.40 |
| H % | 5.97 | 5.95 |
| N % | 13.83 | 13.62 |
| O % | 21.07 | 21.12 |

-continued

| Analysis | Calculated for $C_{12}H_{18}N_3O_4Cl$ | Found |
|---|---|---|
| Cl % | 11.67 | 11.84 |

Second step

Preparation of 2-(β-hydroxypropyl)amino-6-(β-hydroxypropyl)aminonitrobenzene 340 mg of palladium at a concentration of 10% on active charcoal are added to 0.07 mole (21.3 g) of 4-chloro-2-(β-hydroxypropyl)amino-6-(β-hydroxypropyl)aminonitrobenzene in 30 ml of 96° ethanol and 29.2 ml of triethylamine, after which 5.8 ml of formic acid are run in dropwise.

After the end of the addition, the reaction mixture is heated under reflux for 6 hours. The reaction mixture is filtered hot to remove the catalyst. The filtrate, diluted with 200 ml of water, is extracted with ethyl acetate. After drying over sodium sulphate, followed by evaporation of the ethyl acetate, the gum obtained is purified by chromatography on silica and eluted with a 60/40 mixture of cyclohexane and ethyl acetate.

The product obtained melts at 73° C.

Elemental analysis of the product obtained gives the following results:

| Analysis | Calculated for $C_{12}H_{19}N_3O_4$ | Found |
|---|---|---|
| C % | 53.52 | 53.53 |
| H % | 7.11 | 7.10 |
| N % | 15.60 | 15.53 |
| O % | 23.76 | 23.67 |

EXAMPLE 9

Preparation of 2-(β-methoxyethyl)amino-6-(β-methoxyethyl)aminonitrobenzene (Second process)

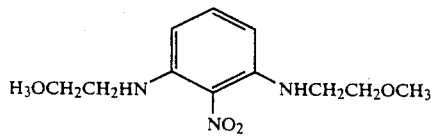

First step

Preparation of 4-chloro-2-(β-methoxyethyl)amino-6-(β-methoxyethyl)aminonitrobenzene

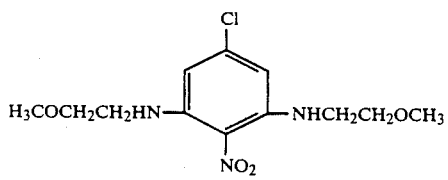

0.2 mole (45.3 g) of 2,4,6-trichloronitrobenzene is added portionwise, with stirring, to 180 ml of 2-methoxyethylamine, heated to 80° C. After the end of the addition the heating is continued for 2 hours 30 minutes. The reaction mixture is diluted with 180 ml of iced water. The expected product precipitates. It is filtered off, washed with water and dried under vacuum at 60° C. in the presence of phosphorus pentoxide. Recrystallized from 96° ethanol, it melts at 90° C.

Analysis of the product obtained gives the following results:

| Analysis | Calculated from $C_{12}H_{18}N_3O_4Cl$ | Found |
|---|---|---|
| C % | 47.45 | 47.49 |
| H % | 5.97 | 6.01 |
| N % | 13.83 | 13.92 |
| O % | 21.07 | 20.91 |
| Cl % | 11.67 | 11.49 |

Second step

Preparation of 2-(β-methoxyethyl)amino-6-(β-methoxyethyl)aminonitrobenzene 0.4 g of palladium at a concentration of 10% on active charcoal is added to 0.084 mole (25.5 g) of 4-chloro-2-(β-methoxyethyl)amino-6-(β-methoxyethyl)aminonitrobenzene in 33.4 ml of triethylamine, after which 7 ml of formic acid are added dropwise. At the end of the additions, the reaction mixture is heated for 1 hour 30 minutes, under reflux. The reaction mixture is diluted with 100 ml of 96° alcohol and 100 ml of water. The expected product precipitates. After filtration, the expected product containing the catalyst is dissolved in 90 ml of isopropyl alcohol. The catalyst is removed by hot filtration. The expected product crystallizes.

It is purified by a preparative chromatography on a $C_{18}$ column (Waters Prep 500 apparatus) and eluted with a mixture of water (40%) and methanol (60%). It melts at 56° C.

Analysis of the product obtained gives the following results:

| Analysis | Calculated for $C_{12}H_{19}N_3)_4$ | Found |
|---|---|---|
| C % | 53.52 | 63.42 |
| H % | 7.11 | 7.10 |
| N % | 15.60 | 15.60 |
| O % | 23.77 | 23.69 |

EXAMPLE 10

Preparation of 2-(β-diethylaminoethyl)amino-6-(β-diethylaminoethyl)aminonitrobenzene dihydrochloride (Second process)

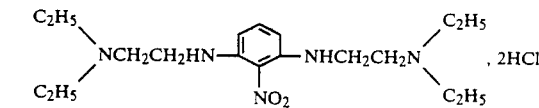

1st step

Preparation of 4-chloro-2-(β-diethylaminoethyl)amino-6-(β-diethylaminoethyl)aminonitrobenzene 0.2 mole (45.3 g) of 2,4,6-trichloronitrobenzene is added portionwise, with stirring, to 180 ml of N,N-diethylethylenediamine, heated to 60° C. After the end of the addition, heating is continued for 30 minutes. The reaction mixture is diluted with 180 ml of iced water. The expected product precipitates. It is filtered off, washed with water and then dried under vacuum at 60° C. in the presence of phosphorus pentoxide. After recrystallization from 96° ethanol, it melts at 90° C.

Analysis of the product obtained gives the following results:

| Analysis | Calculated for $C_{18}H_{32}N_5O_2Cl$ | Found |
|---|---|---|
| C % | 56.02 | 56.02 |
| H % | 8.36 | 8.30 |
| N % | 18.15 | 17.96 |
| O % | 8.29 | 8.46 |
| Cl % | 9.19 | 9.05 |

Second step

Preparation of 2-(β-diethylaminoethyl)amino-6-(β-diethylaminoethyl)aminonitrobenzene dihydrochloride 300 mg of palladium at a concentration of 10% on calcium carbonate are added to 0.015 mole (5.8 g) of 4-chloro-2-(β-diethylaminoethyl)amino-6-(β-diethylaminoethyl)aminonitrobenzene in 11.1 ml of triethylamine, after which 2.86 ml of acetic acid and 2.1 ml of formic acid are added dropwise. After the end of the additions, the materials are heated under reflux for 3 hours 30 minutes. The reaction mixture is diluted with 10 ml of water. The catalyst is removed by hot filtration. The filtrate is evaporated to dryness under vacuum. The inorganic salts are precipitated by adding acetone and are removed by filtration. After evaporation of the acetone, an oil is obtained and this, after treatment with a solution of hydrochloric acid in absolute ethanol, leads to the expected product which is isolated by evaporating off the alcohol and precipitating with ethyl ether.

Analysis of the product obtained gives the following results:

| Analysis | Calculated for $C_{18}H_{35}Cl_2N_5O_2$ | Found |
|---|---|---|
| C % | 50.94 | 50.79 |
| H % | 8.25 | 8.30 |
| N % | 16.51 | 16.59 |
| O % | 7.55 | 7.69 |
| Cl % | 16.74 | 16.71 |

EXAMPLE 11

Preparation of 2-(β-aminoethyl)amino-6-(β-aminoethyl)aminonitrobenzene dihydrochloride (First process)

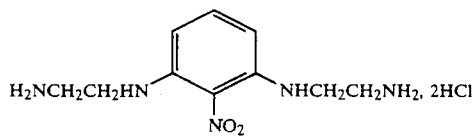

0.16 mole (30 g) of 2,6-dichloronitrobenzene is added to 100 ml of ethylenediamine. The mixture is heated under reflux for 4 hours. The unreacted ethylene diamine is stripped off under vacuum. The expected product is precipitated by adding a 7N solution of hydrochloric acid to the residue obtained.

The product is dissolved in 50 ml of water. After having been filtered to remove an insoluble material, the solution is made alkaline with sodium hydroxide and is extracted with ethyl acetate.

The combined ethyl acetate phases are dried over sodium sulphate. After evaporation of the ethyl acetate under vacuum a residue is obtained. The expected product is precipitated by adding a 7N solution of hydrochloric acid in absolute ethanol.

Analysis of the purified product gives the following results:

| Analysis | Calculated for $C_{10}H_{19}Cl_2N_5O_2$ | Found |
|---|---|---|
| C % | 38.46 | 38.50 |
| H % | 6.09 | 6.10 |
| N % | 22.43 | 22.53 |
| O % | 10.25 | 10.41 |
| Cl % | 22.76 | 22.76 |

APPLICATION EXAMPLE 1

The following dyeing mixture is prepared:

| | |
|---|---|
| 2,6-Diaminonitrobenzene | 0.1 g |
| 2-Butoxyethanol | 10 g |
| Cellosize W.P. 03 - Union Carbide Company (hydroxyethylcellulose) | 2 g |
| Cetyldimethylhydroxyethylammonium chloride | 2 g |
| 5% strength aqueous ammonia | 0.9 g |
| Water q.s. | 100 g |
| pH: 10 | |

This mixture, applied to bleached hair for 30 minutes at 28° C. imparts a light salmon color to it, after shampooing and rinsing.

APPLICATION EXAMPLE 2

The following dyeing mixture is prepared:

| | |
|---|---|
| 2-(β-hydroxyethyl)amino-6-(β-hydroxyethyl)-aminonitrobenzene | 0.1 g |
| 2-Butoxyethanol | 10 g |
| Cellosize W.P. 03 Union Carbide Company (hydroxyethylcellulose) | 2 g |
| Ammonium lauryl sulphate | 5 g |
| 5% strength aqueous ammonia | 0.9 g |
| Water q.s. | 100 g |
| pH: 9 | |

This mixture, applied to 90% naturally white hair for 30 minutes at 28° C. imparts a silvery light pink color to it, after shampooing and rinsing.

APPLICATION EXAMPLE 3

The following dyeing mixture is prepared:

| | |
|---|---|
| 2-Amino-6-methylaminonitrobenzene | 0.25 g |
| 2-Butoxyethanol | 5 g |
| Propylene glycol | 5 g |
| Alfol C 16/18 - Condea Company (cetylstearyl alcohol) | 8 g |
| | 8 g |
| Lanette Wax E - Henkel Company (sodium cetylstearyl sulphate) | 0.5 g |
| | 0.5 g |
| Cémulsol B - Rhône-Poulenc Company (ethoxylated castor oil) | 1 g |
| Oleoyldiethanolamide | 1.5 g |
| Water q.s. | 100 g |
| pH: 7.3 | |

This mixture, applied to bleached hair for 20 minutes at 27° C, imparts a purplish-blue-pink color to it, after shampooing and rinsing.

APPLICATION EXAMPLE 4

Oxidation dye

The following dyeing mixture is prepared:

| | |
|---|---|
| 2,6-Diaminonitrobenzene | 0.3 g |
| p-Aminophenol | 0.05 g |
| Resorcin | 0.08 g |
| 4-Amino-3-hydroxytoluene | 0.08 g |
| (N,N-di-β-hydroxyethyl)aminoaniline sulphate | 0.19 g |
| 96° ethanol | 10 g |
| Cémulsol NP 4 - Rhône-Poulenc (nonylphenol oxyethylenated with 4 moles of ethylene oxide) | 12 g |
| Cémulsol NP 9 - Rhône-Poulenc (nonylphenol oxyethylenated with 9 moles of ethylene oxide) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |
| Trilon B (ethylenediaminetetraacetic acid) | 0.12 g |
| 22° Bé aqueous ammonia | 11 g |
| Thioglycolic acid | 0.6 g |
| Water q.s. | 100 g |
| pH: 10.6 | |

120 g of 20-volume hydrogen peroxide are added at the time of use. The mixture, applied to natural grey hair for 20 minutes at 27° C, imparts an ashen, very light chestnut-brown color to it, after shampooing and rinsing.

APPLICATION EXAMPLE 5

The following dyeing mixture is prepared:

| | |
|---|---|
| 2,6-Diaminonitrobenzene | 0.25 g |
| 3-Nitro-4-N'-(β-hydroxyethyl)amino-N,N-(di-β-hydroxyethyl)aniline | 0.45 g |
| (3-Methylamino-4-nitro)phenoxy ethanol | 0.25 g |
| 2-Butoxy ethanol | 10 g |
| Cémulsol NP 4 - Rhône-Poulenc Company (nonylphenol with 4 moles of ethylene oxide) | 12 g |
| Cémulsol NP 9 - Rhône-Poulenc Company (nonylphenol with 9 moles of ethylene oxide) | 15 g |
| Oleyl alcohol polyglycerolated with 2 moles of glycerol | 1.5 g |
| Oleyl alcohol polyglycerolated with 4 moles of glycerol | 1.5 g |
| Monoethanolamine as 20% strength by weight aqueous solution | 2 g |
| Water q.s. | 100 g |
| pH: 9.5 | |

This mixture, applied to natural grey hair for 20 minutes at 30° C, imparts an ash-blonde color to it, after shampooing and rinsing.

APPLICATION EXAMPLE 6

The following dyeing mixture is prepared:

| | |
|---|---|
| 2-(β-Hydroxyethyl)amino-6-(β-hydroxyethyl)aminonitrobenzene | 0.25 g |
| 3-Nitro-4-N'-(γ-hydroxypropyl)amino-N,N-(di-β-hydroxyethyl)aniline | 0.30 g |
| (3-Methylamino-4-nitro)phenyl β,γ-dihydroxypropyl ether | 0.2 g |
| Carbopol 934 - Goodrich Chemicals Company (polyacrylic acid crosslinked with a polyfunctional agent) | 2 g |
| Ethanol | 10 g |
| Triethanolamine | 5 g |
| Water q.s. | 100 g |
| pH: 7.5 | |

This mixture, applied to bleached hair for 25 minutes at 27° C, imparts a pink-marron glace color to it, after shampooing and rinsing.

APPLICATION EXAMPLE 7

The following dyeing mixture is prepared:

| | |
|---|---|
| 2-Amino-6-methylaminonitrobenzene | 0.1 g |
| 2,6-Diamino-4-chloronitrobenzene | 0.4 g |
| 2-(β-hydroxyethyl)amino-4-(β-hydroxyethyl)amino-5-chloronitrobenzene | 0.2 g |
| 1,4,5,8-Tetraaminoanthraquinone | 0.14 g |
| Ethanol | 15 g |
| Cémulsol NP 4-Rhône-Poulenc Company (nonylphenol with 4 moles of ethylene oxide) | 12 g |
| Cémulsol NP 9-Rhône-Poulenc Company (nonylphenol with 9 moles of ethylene oxide) | 15 g |
| Oleyl alcohol polyglycerolated with 2 moles of glycerol | 1.5 g |
| Oleyl alcohol polyglycerolated with 4 moles of glycerol | 1.5 g |
| 1% strength aqueous triethanolamine | 1.3 g |
| Water q.s. | 100 g |
| pH: 9 | |

This mixture, applied to bleached hair for 25 minutes at 30° C, imparts a golden blonde color to it, after shampooing and rinsing.

APPLICATION EXAMPLE 8

Oxidation dye

The following dyeing mixture is prepared:

| | |
|---|---|
| 2,6-Diaminonitrobenzene | 1 g |
| para-Phenylenediamine | 0.1 g |
| para-Aminophenol | 0.07 g |
| meta-Aminophenol | 0.12 g |
| (2,4-Diamino)phenoxyethanol dihydrochloride | 0.06 g |
| 4-N-methylaminophenol hemisulphate | 0.12 g |
| Alfol C 16/18-Condea Company (cetylstearyl alcohol) | 8 g |
| Lanette Wax E-Henkel Company (sodium cetylstearylsulphate) | 0.5 g |
| Cémulsol B-Rhône-Poulenc (ethoxylated castor oil) | 1 g |
| Oleyldiethanolamine | 1.5 g |
| Masquol DTPA-Protex Company (pentasodium diethylenetriaminepentaacetate) | 2.5 g |
| 22° Bé aqueous ammonia | 11 g |
| Water q.s. | 100 g |
| pH 10.2 | |

100 g of 20-volume hydrogen peroxide are added at the time of use. The mixture, applied to 90% naturally white hair for 25 minutes at 38° C., imparts a coppery, medium chestnut-brown color to it, after shampooing and rinsing.

APPLICATION EXAMPLE 9

Oxidation dye

The following dyeing mixture is prepared:

| | |
|---|---|
| 2-(β-Hydroxyethyl)amino-6-(β-hydroxyethyl)aminonitrobenzene | 0.6 g |
| para-Phenylene diamine | 0.06 g |
| para-Aminophenol | 0.5 g |
| meta-Aminophenol | 0.4 g |
| Resorcin | 0.4 g |
| 4-(β-Hydroxyethyl)amino-2-hydroxytoluene | 0.1 g |
| Cémulsol NP4-Rhône-Poulenc Company (nonylphenol with 4 moles of ethylene oxide) | 21 g |
| Cémulsol NP9-Rhône-Poulenc Company (nonylphenol with 9 moles of ethylene oxide) | 24 g |

-continued

| Oleic acid | 4 g |
|---|---|
| Butylglycol | 3 g |
| 96° ethanol | 10 g |
| Masquol DTPA-Protex (pentasodium di-ethylenetriaminepentaacetate) | 2.5 g |
| 35° Bé Socium hydrogen sulphite solution | 1 g |
| Aqueous ammonia | 10 g |
| Water q.s. | 100 g |
| pH: 10.5 | |

100 g of 20-volume hydrogen peroxide are added at the time of use. The mixture, applied to 90% naturally white hair for 20 minutes at 38° C., imparts a coppery light chestnut-brown color to it, after shampooing and rinsing.

APPLICATION EXAMPLE 10

The following dyeing mixture is prepared:

| 2-Amino-6-($\beta$-hydroxyethyl)aminonitrobenzene | 0.5 g |
|---|---|
| 2-Butoxyethanol | 15 g |
| Cellosize W.P. 03-Union Carbide Company (hydroxyethylcellulose) | 2 g |
| Cetyldimethylhydroxyethylammonium chloride | 2 g |
| Water q.s. | 100 g |
| pH: 11 | |

This mixture, applied to natural grey hair for 30 minutes at 30° C., imparts a light red color to it, after shampooing and rinsing.

APPLICATION EXAMPLE 11

The following dyeing mixture is prepared:

| 2-($\beta$-Hydroxypropyl)amino-6-($\gamma$-hydroxypropyl)-aminonitrobenzene | 0.25 g |
|---|---|
| 96° alcohol | 9 g |
| Carbopol 934-Goodrich Chemicals Company (crosslinked polyacrylic acid) | 2 g |
| Triethanolamine | 3 g |
| Water q.s. | 100 g |
| pH: 8.3 | |

This mixture, applied to 90% naturally white hair for 25 minutes at 35° C., imparts a slightly grey red color to it, after shampooing and rinsing.

APPLICATION EXAMPLE 12

The following dyeing mixture is prepared:

| 2-($\beta$-Hydroxypropyl)amino-6-($\beta$-hydroxypropyl)-aminonitrobenzene | 0.26 g |
|---|---|
| 2-Butoxyethanol | 10 g |
| Alfol C 16/18-Condea Company (cetylstearyl alcohol) | 8 g |
| Lanette Wax E-Henkel Company (sodium cetylstearyl sulphate) | 0.5 g |
| Cémulsol B-Rhône-Poulenc Company (ethoxylated castor oil) | 1 g |
| Oleoyldiethanolamide | 1.5 g |
| Triethanolamine | 4 g |
| Water q.s. | 100 g |
| pH: 9.4 | |

This mixture, applied to bleached hair for 25 minutes at 35° C., imparts a grey purple-red color it, after shampooing and rinsing.

APPLICATION EXAMPLE 13

The following dyeing mixture is prepared:

| 2-($\beta,\gamma$-Dihydroxypropyl)amino-6-($\beta,\gamma$-dihydroxypropyl)aminonitrobenzene | 0.238 g |
|---|---|
| Propylene glycol | 12 g |
| Cellosize W.P. 03-Union Carbide Company (hydroxyethylcellulose) | 2 g |
| Cetyldimethylhydroxyethylammonium chloride | 2 g |
| 20% strength aqueous ammonia solution | 3 g |
| Water q.s. | 100 g |
| pH: 10.4 | |

This mixture, applied to permanent-waved hair for 30 minutes at 35° C. imparts a slightly grey red color to it, after shampooing and rinsing.

APPLICATION EXAMPLE 14

The following dyeing mixture is prepared:

| 2-($\beta$-Methoxyethyl)amino-6-($\beta$-methoxyethyl)-aminonitrobenzene | 0.105 g |
|---|---|
| Propylene glycol | 10 g |
| Alfol C 16/18-Condea Company (cetylstearyl alcohol) | 8 g |
| Lanette Wax E-Henkel Company (sodium cetylstearylsulphate) | 0.5 g |
| Cémulsol B-Rhône-Poulenc Company (ethoxylated castor oil) | 1 g |
| Oleoyldiethanolamide | 1.5 g |
| 20% strength aqueous ammonia solution | 2 g |
| Water q.s. | 100 g |
| pH: 10 | |

This mixture, applied to permanent-waved hair for 25 minutes at 35° C., imparts a slightly grey, light red-brown color to it, after shampooing and rinsing.

APPLICATION EXAMPLE 15

The following dyeing mixture is prepared:

| 2-($\beta$-Diethylaminoethyl)amino-6-($\beta$-diethyl-aminoethyl)aminonitrobenzene | 0.17 g |
|---|---|
| Propylene glycol | 10 g |
| Alfol C 16/18-Condea Company (cetylstearyl alcohol) | 8 g |
| Lanette Wax E-Henkel Company (sodium cetylstearylsulphate) | 0.5 g |
| Cémulsol B-Rhône-Poulenc Company (ethoxylated castor oil) | 1 g |
| Oleoyldiethanolamide | 1.5 g |
| 20% strength aqueous ammonia solution | 5 g |
| Water q.s. | 100 g |
| pH: 10 | |

This mixture, applied to bleached hair for 35 minutes at 35° C., imparts a light yellow-brown color to it, after shampooing and rinsing.

APPLICATION EXAMPLE 16

The following dyeing mixture is prepared:

| 2-($\beta$-Hydroxyethoxyethyl)amino-6-($\beta$-hydroxyethoxyethyl)aminonitrobenzene | 0.10 g |
|---|---|
| 2-Butoxyethanol | 11 g |
| Cellosize W.P. 03-Union Carbide Company (hydroxyethylcellulose) | 2 g |
| Cetyldimethylhydroxyethylammonium chloride | 2 g |
| Monoethanolamine | 6 g |
| Water q.s. | 100 g |

This mixture, applied to permanent-waved hair for 25 minutes at 35° C., imparts a light grey red-brown color to it, after shampooing and rinsing.

APPLICATION EXAMPLE 17

Oxidation dye

The following dyeing mixture is prepared:

| | |
|---|---|
| 2-(γ-Hydroxypropyl)amino-6-(γ-hydroxypropyl)-aminonitrobenzene | 1.5 g |
| para-Phenylenediamine | 0.1 g |
| para-Aminophenol | 0.07 g |
| meta-Aminophenol | 0.14 g |
| (2,4-Diamino)phenoxyethanol dihydrochloride | 0.06 g |
| 4-N-methylaminophenol hemisulphate | 0.13 g |
| Alfol C 16/18-Condea Company (cetylstearyl alcohol) | 8 g |
| Lanette Wax E-Henkel Company (sodium cetylstearylsulphate) | 0.5 g |
| Cémulsol B-Rhône-Poulenc (ethoxylated castor oil) | 1 g |
| Oleoyldiethanolamide | 1.5 g |
| Masquol DTPA-Protex Company (pentasodium diethylenetriaminepentaacetate) | 2.5 g |
| 22° Bé aqueous ammonia | 11 g |
| Water q.s. | 100 g |
| pH: 10 | |

100 g of 20-volume hydrogen peroxide are added at the time of use. The mixture, applied to 90% white hair for 25 minutes at 38° C., imparts a purple-violet light chestnut-brown color to it, after shampooing and rinsing.

APPLICATION EXAMPLE 18

Oxidation dye

The following dyeing mixture is prepared:

| | |
|---|---|
| 2-Amino-6-(β-hydroxyethyl)aminonitrobenzene | 0.6 g |
| para-Phenylenediamine | 0.06 g |
| para-Aminophenol | 0.5 g |
| meta-Aminophenol | 0.4 g |
| Resorcin | 0.4 g |
| 4-(β-hydroxyethyl)amino-2-hydroxytoluene | 0.1 g |
| Cémulsol NP4-Rhône-Poulenc (nonylphenol with 4 moles of ethylene oxide) | 21 g |
| Cémulsol NP9-Rhône-Poulenc (nonylphenol with 9 moles of ethylene oxide) | 24 g |
| Oleic acid | 4 g |
| 2-butoxyethanol | 3 g |
| 96° ethanol | 10 g |
| Masquol DTPA-Protex (pentasodium diethylenetriaminepentaacetate) | 2.5 g |
| 35° Bé sodium bisulphite solution | 1 g |
| Aqueous ammonia | 10 g |
| Water q.s. | 100 g |
| pH: 10.3 | |

100 g of 20-volume hydrogen peroxide are added at the time of use. The mixture, applied to 90% naturally white hair for 20 minutes at 38° C., imparts a coppery, very light chestnut-brown color to it, after shampooing and rinsing.

APPLICATION EXAMPLE 19

Oxidation dye

The following dyeing mixture is prepared:

| | |
|---|---|
| 2-(β,γ-dihydroxypropyl)amino-6-(β,γ-dihydroxypropyl)aminonitrobenzene | 0.5 g |
| p-Aminophenol | 0.05 g |
| Resorcin | 0.08 g |
| 4-Amino-2-hydroxytoluene | 0.08 g |
| (N,N-di-β-hydroxyethyl)aminoaniline sulphate | 0.19 g |
| 96° ethanol | 10 g |
| Cemulsol NP 4-Rhone-Poulenc (nonylphenol-oxyethylenated with 4 moles of ethylene oxide) | 12 g |
| Cemulsol NP 9-Rhone-Poulenc (nonylphenol-oxyethylenated with 9 moles of ethylene oxide) | 15 g |
| Oleyl alcohol polyglycerolated with 2 moles of glycerol | 1.5 g |
| Oleyl alcohol polyglycerolated with 4 moles of glycerol | 1.5 g |
| Propylene glycol | 6 g |
| Trilon B (ethylenediaminetetraacetic acid) | 0.12 g |
| 22° Be aqueous ammonia | 11 g |
| Thioglycolic acid | 0.6 g |
| Water q.s. | 100 g |
| pH: 10.6 | |

120 g of 20-volume hydrogen peroxide are added at the time of use. The mixture, applied to 90% white hair for 20 minutes at 27° C., imparts a coppery, light blonde color to it, after shampooing and rinsing.

We claim:

1. A process for preparing a compound having the formula

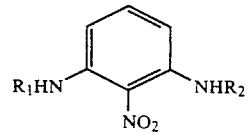

wherein
R$_1$ and R$_2$, each independently, represent hydrogen, alkyl containing 1-6 carbon atoms, monohydroxyalkyl containing 1-6 carbon atoms, polyhydroxyalkyl containing 1-6 carbon atoms, alkoxyalkyl wherein the alkyl moiety contains 1-6 carbon atoms, hydroxyalkoxyalkyl wherein the alkyl moiety contains 1-6 carbon atoms or aminoalkyl wherein the alkyl moiety contains 1-6 carbon atoms and wherein the amino moiety is unsubstituted or substituted with 1-2 alkyl or hydroxyalkyl groups wherein said alkyl has 1-6 carbon atoms or wherein the nitrogen atom of said aminoalkyl forms part of a heterocycle, said process comprising dehalogenating a compound of the formula

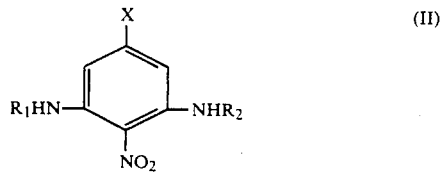

wherein X halogen and R$_1$ and R$_2$ have the meanings given above, with triethylamine formate in the presence of palladium on a support without involving the simultaneous reduction of the nitro group, said support being selected from the group consisting of barium sulfate, barium carbonate, alumina and calcium carbonate.

2. The process of claim 1 wherein a solvent is present.

3. The process of claim 2 wherein said solvent is an alcohol, dimethylformamide, N-methylpyrrolidone or acetic acid.

4. The process of claim 1 wherein the compound of formula II, wherein $R_1$ and $R_2$ are identical and are other than hydrogen, is prepared by reacting a 2,4,6-trihalonitrobenzene having the formula

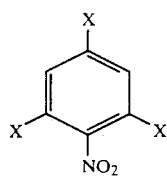

wherein X is halogen with an amine having the formula $NH_2R_1$ wherein $R_1$ has the meaning given in claim 34 with the proviso that $R_1$ is not hydrogen at a temperature ranging from 10° C. to the reflux temperature of the amine of formula $NH_2R_1$ or of any solvent present.

5. The process of claim 4 carried out in an autoclave at a maximum pressure of 25 kg/cm² when said amine of formula $NH_2R_1$ has a boiling temperature lower than or equal to ambient temperature.

6. A process for preparing a 2-nitro metaphenylenediamine compoud having the formula

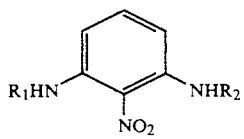

wherein $R_1$ and $R_2$ are different and each, independently, represent hydrogen, alkyl containing 1-6 carbon atoms, monohydroxyalkyl containing 1-6 carbon atoms, polyhydroxyalkyl containing 1-6 carbon atoms, alkoxyalkyl wherein the alkyl moiety contains 1-6 carbon atoms, hydroxyalkoxyalkyl wherein the alkyl moiety contains 1-6 carbon atoms, or aminoalkyl wherein the alkyl moiety contains 1-6 carbon atoms and wherein the amino moiety is unsubstituted or substituted with 1-2 alkyl or hydroxyalkyl groups wherein said alkyl has 1-6 carbon atoms or wherein the nitrogen atom of said aminoalkyl forms part of a heterocycle, said process comprising, in a first step, reacting a 2,4,6-trihalonitrobenzene having the formula

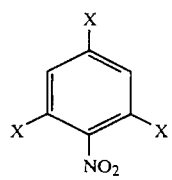

wherein X is halogen with ammonia or an amine of the formula $NH_2R_1$ wherein $R_1$ has the meaning given above to produce a compound having the formula

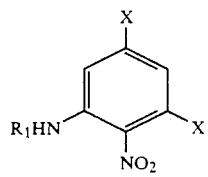

in a second step, reacting said compound having formula (V) with ammonia or an amine of the formula $NH_2R_2$ wherein $R_2$ has the meaning given above, the reaction in both said first and second steps being carried out at a temperature ranging from 10° C. to the reflux temperature of the ammonia or amine present or of any solvent present to produce a compound having the formula

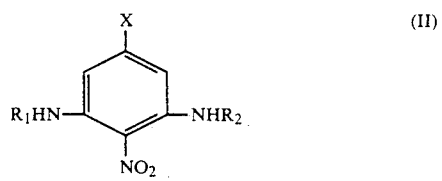

wherein $R_1$ and $R_2$ have the meaning given above and X is halogen, and in a third step, dehalogenating said compound having formula (II) with triethylamine formate in the presence of palladium on a support, said support being selected from the group consisting of barium sulfate, barium carbonate, alumina and calcium carbonate.

7. A process for preparing a compound having the formula

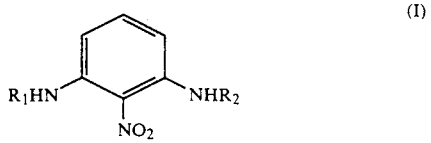

wherein $R_1$ and $R_2$, each independently, represent hydrogen, alkyl containing 1-6 carbon atoms, monohydroxyalkyl containing 1-6 carbon atoms, polyhydroxyalkyl containing 1-6 carbon atoms, alkoxyalkyl wherein the alkyl moiety contains 1-6 carbon atoms, hydroxyalkoxyalkyl wherein the alkyl moiety contains 1-6 carbon atoms, or aminoalkyl wherein the alkyl moiety contains 1-6 carbon atoms and wherein the amino moiety is unsubstituted or substituted with 1-2 alkyl or hydroxyalkyl groups wherein said alkyl has 1-6 carbon atoms or wherein the nitrogen atom of said aminoalkyl forms part of a heterocycle, said process comprising dehalogenating a compound of the formula

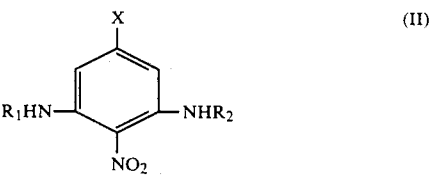

wherein X is halogen and $R_1$ and $R_2$ have the meanings given above with triethylamine formate, the dehalogenation reaction being carried out with palladium on calcium carbonate or palladium on barium carbonate without involving the simultaneous reduction of the nitro group, in the presence of acetic acid, formic acid and triethylamine.

* * * * *